United States Patent [19]

Albrektsson et al.

[11] Patent Number: 5,443,516
[45] Date of Patent: Aug. 22, 1995

[54] JOINT PROSTHESIS

[76] Inventors: Björn Albrektsson, Sveagatan 11, Göteborg, Sweden, S-413 14; Stig Wennberg, Villa Holma 6266, Angered, Sweden, S-424 57

[21] Appl. No.: 197,679

[22] Filed: Feb. 17, 1994

Related U.S. Application Data

[63] Continuation of Ser. No. 768,779 filed as PCT/SE90/00215, Apr. 3, 1990, abandoned.

[30] Foreign Application Priority Data

Apr. 11, 1989 [SE] Sweden ............... 8901315

[51] Int. Cl.⁶ ............... A61F 2/30; A61F 2/42
[52] U.S. Cl. .................. 623/18; 623/21; 606/70; 606/71
[58] Field of Search ............ 606/60, 65, 69, 70, 606/71; 623/21, 18 (U.S. Only), 23, 22, 20, 16

[56] References Cited

U.S. PATENT DOCUMENTS

| | | | |
|---|---|---|---|
| 3,670,724 | 6/1972 | Bosacco | 606/71 X |
| 3,987,499 | 10/1976 | Scharbach et al. | 623/22 |
| 4,059,102 | 11/1977 | Devas | 606/69 X |
| 4,131,957 | 1/1979 | Bokros | 623/21 X |
| 4,262,368 | 4/1981 | Lacey | 623/20 |
| 4,578,081 | 3/1986 | Harder et al. | 623/22 |
| 4,655,778 | 4/1987 | Koeneman | 623/21 |
| 4,795,473 | 1/1989 | Grimes | 623/23 |
| 4,838,891 | 6/1989 | Branemark et al. | 623/20 |
| 4,840,632 | 6/1989 | Kampner | 623/22 |
| 4,865,607 | 9/1989 | Witzel et al. | 623/20 |
| 4,936,853 | 6/1990 | Fabian et al. | 623/20 |

FOREIGN PATENT DOCUMENTS

| | | | |
|---|---|---|---|
| 0475358 | 3/1992 | European Pat. Off. | 623/18 |
| 2433932 | 3/1980 | France | 623/23 |
| 2478462 | 9/1981 | France | 623/18 |
| 2550936 | 3/1985 | France | 623/18 |
| 2576793 | 8/1986 | France | 623/18 |
| 2589353 | 5/1987 | France | 623/23 |
| 2114323 | 10/1971 | Germany | 623/18 |
| 3315401 | 10/1984 | Germany | 623/20 |
| 3429157 | 2/1986 | Germany | 623/20 |
| 2070939 | 9/1981 | United Kingdom | 623/18 |
| 0719625 | 3/1980 | U.S.S.R. | 623/20 |
| 0923532 | 4/1982 | U.S.S.R. | 606/71 |
| 1311727 | 5/1987 | U.S.S.R. | 606/70 |
| 1438752 | 11/1988 | U.S.S.R. | 606/60 |
| 1734727 | 5/1992 | U.S.S.R. | 623/20 |
| 8502535 | 6/1985 | WIPO | 623/18 |
| 9107931 | 6/1991 | WIPO | 623/18 |

*Primary Examiner*—David H. Willse
*Attorney, Agent, or Firm*—Lerner, David, Littenberg, Krumholz & Mentlik

[57] ABSTRACT

A joint prosthesis is disclosed. The joint prosthesis is preferably used for small joints, such as finger joints, and comprises at least one distal prosthesis element and at least one proximal prosthesis element. A joint is arranged between the distal and proximal prosthesis elements to allow for articulated movement therebetween. The distal and proximal prosthesis elements are secured to corresponding distal and proximal bone shafts.

20 Claims, 5 Drawing Sheets

JOINT PROSTHESIS

This is a continuation of application Ser. No. 07/768,779 filed Oct. 9, 1991, now abandoned.

TECHNICAL FIELD

The present invention relates to a joint prosthesis, which permits permanent anchoring in human joints. The joint is primarily intended to be used on small joints such as finger-joints. However, it is not limited to these, but can also be used on large joints such as elbow-joints or knee-joints.

PRIOR ART AND PROBLEMS

On the market today there is essentially one type of finger-joint prosthesis of the kind known from DE A 3 008 292. This is made of silicone plastic and is applied in the medullary cavity of the bone proximally and distally of the joint in question. The middle section of the prosthesis has a waist, which is designed to increase the flexibility in the middle of the joint. The ends of the bones facing the joint are cut away in the operation, and the prosthesis is introduced into the medullary cavity. The ends of the prosthesis thus move relatively freely in each medullary cavity in the axial direction during movements in the joint. The prosthesis is thus not anchored against the bones. In many cases this movement produces, after a certain time, on account of inadequate physiological loading, attrition of the cortex which surrounds the medullary cavity. This results in an increased risk of fracture formation in the bone shafts. An advantage of the present method is the relatively uncomplicated surgical technique.

One problem, besides the risk of local attrition of bone, is that the stability in the joint remains poor after the operation since the construction of the prosthesis precludes lateral stability on account of the use of silicone plastic which is soft and yielding. In addition, the use of silicone can, due to wearing off of silicone fragments, give rise to cyst formations.

The patients who nowadays mainly receive finger-joint prostheses are those with degenerative finger-joint diseases such as rheumatoid arthritis, and patients with traumatic finger-joint injuries. The indications for surgery are mainly pain and inadequate ability to use the fingers as a result of poor stability in the finger-joints. Since the risks of the bone suffering local attrition and of the stability after the operation not being optimal are nowadays relatively great, finger-joint prostheses are mainly reserved for very serious cases of finger-joint disease where the requirements regarding usability have not been set particularly high. This means that it is primarily the elderly and severely handicapped who predominantly undergo surgery, since these patients are expected to have a lower activity level and a shorter remaining lifetime. The large group of patients under 60 years of age with serious symptoms and at the same time with relatively high requirements for usability may not undergo surgery for finger-joint prostheses due to the doubts regarding the reliability of the joint replacements on offer today with respect to their long-term results and the usability of the operated finger-joint.

There is at present a Swedish method for skeletal anchoring of dental bridges with dental implants, where the anchoring stability is initially good and can be maintained for over 20 years following the skeletal implantation. This unique anchoring stability for the skeletal implant is probably dependent on establishing a contact, free of connective tissue, between the bone tissue and the implant, so-called osseointegration. The preconditions for an anchoring situation of this type have been stated as being the use of biocompatible materials with high corrosion resistance, such as commercially pure titanium, combined with a controlled non-traumatic surgical method and the avoidance of direct loading by means of the implant being introduced in a two-stage procedure, where only an anchoring element is implanted in the first stage, and it is only in a second operation that a loaded function element is added.

In addition, there is now wide experience of the use of ceramic materials for implantation in body tissues. The ceramics are characterized by rigidity combined with great corrosion resistance and no output of substances injurious to the body.

SOLUTION AND ADVANTAGES

The aim of the present invention is to provide a joint prosthesis which builds on the experience gained from the abovementioned Swedish method for jaw implantation and which eliminates the disadvantages which are associated with the use of the teaching known from DE A 3 008 292, which discloses a joint prosthesis, preferably for small joints such as finger-joints, comprising at least one distal prosthesis element and at least one proximal prosthesis element, a joint by means of which the said prosthesis elements are connected in an articulated manner, and securing means for securing the said distal part on the distal bone shaft of the joint and the said proximal part on the proximal bone shaft of the joint.

The said aim is achieved by means of an arrangement according to the present invention, which is characterized in that at least one of the said prosthesis elements has at least one attachment part which can be applied on the periosteal part of the bone shaft on which it is intended to be attached which attachment part has at least one through passage and that at least one of said securing means comprises at least one first anchoring member, which can be fitted in one of said bone shafts and which interacts with at least one second anchoring member, whereby both of said anchoring members interact with said through passage for fixation of said attachment part on said bone shaft.

A further aim of the present invention is to produce a joint prosthesis by means of which the surgical defect upon prosthetic surgery is reduced, that is to say the cutting away of intact bone tissue can be reduced in connection with the operation by means of the fact that only the joint head, the proximal joint end, need be cut away, and which in its preferred embodiment does not require any further cutting of spongy osseous tissue.

The present invention aims to create the preconditions for a satisfactory anchoring stability, which means that it is possible to extend the range of indications for joint surgery, in particular finger-joint surgery, to more active persons of younger age groups and to afford greater joint stability than is now the case.

DESCRIPTION OF FIGURES

The invention will be illustrated in greater detail below on the basis of exemplary embodiments and with reference to the attached drawings, in which.

PREFERRED EMBODIMENTS

Figure 1:
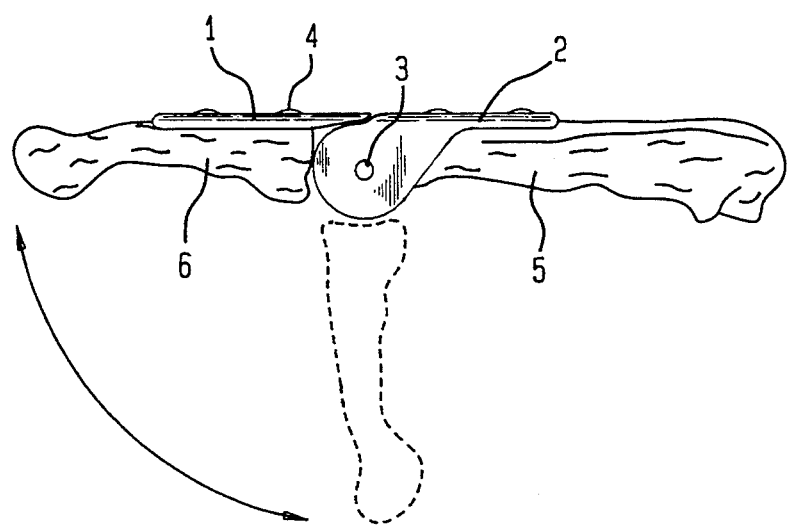
FIG. 1 shows a side view of the prosthesis implanted in a finger-joint.

FIG. 1 thus shows a prosthesis in accordance with the invention, which has been implanted in a finger-joint. The joint prosthesis shown consists of a distal prosthesis element 1 which is secured on the distal bone shaft 6 of the joint by securing means 4, a proximal prosthesis element 2 which is secured on the proximal bone shaft 5 of the joint by securing means 4, and a joint 3 by means of which the said prosthesis elements 1, 2 are connected in an articulated manner. The broken line in FIG. 1 shows how the distal part 6 of the joint can pivot about the joint 3 of the prosthesis.

Figure 2:
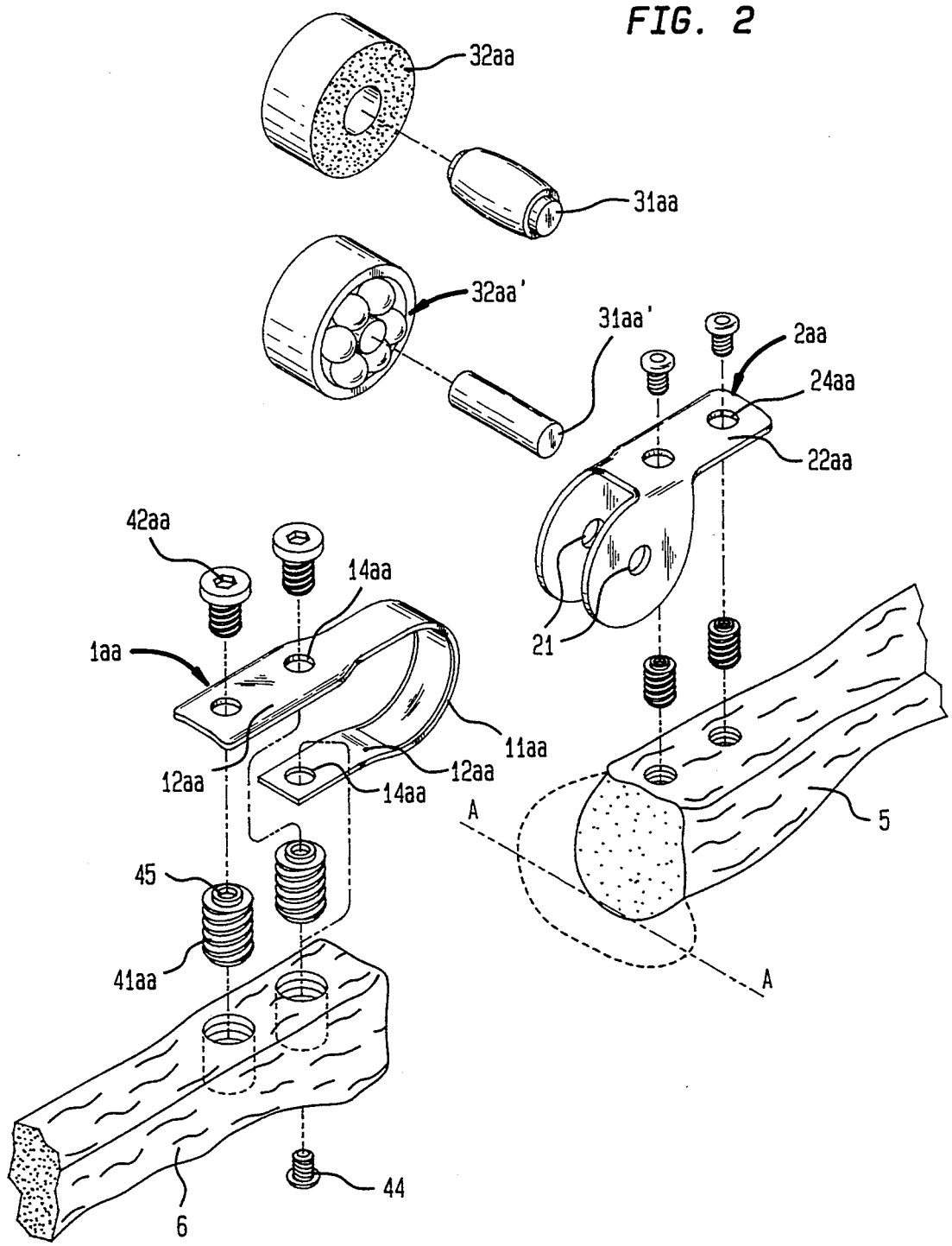
FIG. 2 shows an exploded view of a preferred embodiment of the invention.

FIG. 2 shows the construction of a preferred form of a prosthesis according to the invention and how it is intended to be secured. The distal prosthesis part 1 here consists of a band-shaped material. A 0.5 mm titanium plate has been found to be very suitable for this purpose, but other biocompatible materials with corresponding strength characteristics are also conceivable, such as reinforced polymer material. This distal part is provided with an upper and a lower attachment part 12aa provided with holes 14aa.

This distal part 1aa is moreover intended to be provided with means 11aa for fixing the outer part of a bearing member 32aa. This is preferably achieved by means of the fact that the band-shaped material is allowed essentially to surround the outer circular surface of the bearing member 32aa. For anchoring of the distal prosthesis element 1aa, there are anchoring members 41aa which preferably consist of two through titanium screws which are provided with internal threads. Coaxial to these internal threads there is a raised part 45 whose thickness at least approximately corresponds to the thickness of the band-shaped material of the prosthesis element, and the holes 14aa which are arranged in the attachment parts 12aa, 22aa of the prosthesis element have a diameter which corresponds to the diameter of the said raised part 45. In this way tensile loads in the prosthesis can be transferred directly to the said anchoring members 41aa via the said raised parts 45, so that the dimension of the securing members 42aa can be kept down.

When the prosthesis element is mounted on the anchoring members 41aa, this is achieved suitably by means of screws 42aa which are screwed into the internal thread of the anchoring member 41aa. As emerges from FIG. 2, both anchoring members 41aa are of the through type, but only one of them has to be designed with internal threads at both end surfaces, since one end of the attachment parts of the distal prosthesis element 1aa is secured with a downward-directed screw 42aa in the said anchoring member 41, while the other end of the prosthesis element is secured by means of an upward-directed screw 44 in the same anchoring member 41aa.

In order to make space for the distal prosthesis element 1aa, it is in most cases not necessary to carry out any cutting of the distal bone shaft 6. However, a slight scraping may be necessary in order to better fit the prosthesis element. As emerges from FIG. 2, the joint head has been cut away from the proximal bone shaft 5, which is necessary in order to make space for the prosthesis. The proximal prosthesis element is attached in principle in the same way as the distal part 1aa, but the proximal prosthesis element has only one attachment part 22aa. This attachment part 22aa is provided with two holes 24aa which, in a manner corresponding to the distal part, cooperate with securing members 41aa. The proximal prosthesis element is moreover provided with two coaxial hollows 21 which are intended to cooperate with an axle element 31aa in the joint 3.

FIG. 2 shows two alternative embodiments including bearing members 32aa and 32aa1 which can be used in the joint prosthesis. The lower of these alternatives has a ball or roller bearing 32aa1, advantageously made of a ceramic, which is intended to be mounted on an axle element 31aa1. In the second alternative there is a slide bearing, again advantageously made of ceramic material. In this case it is intended that the axle element 31aa1 should preferably be integrated with the bearing body 32aa1 (but not necessarily). As can be seen, this slide bearing has a slightly spherical outer surface, by which means it is possible for a prosthesis joint to be given a certain desired and controlled lateral movement. Even if a joint essentially free from play is desirable, it is an additional advantage if such a joint affords a certain lateral movement, as in a physiological joint.

In the preferred form of the invention, the anchoring elements 41aa and the function elements are introduced in separate operation stages, with an intermediate load-free period of at least 3 months. Upon implantation of the function elements, the distal part 1aa is attached in such a way that its intermediate part 11aa essentially surrounds and fixes the bearing member 32aa which is mounted on the axle element 31aa which in turn is positionally fixed on the proximal prosthesis element 2aa.

Figure 3:
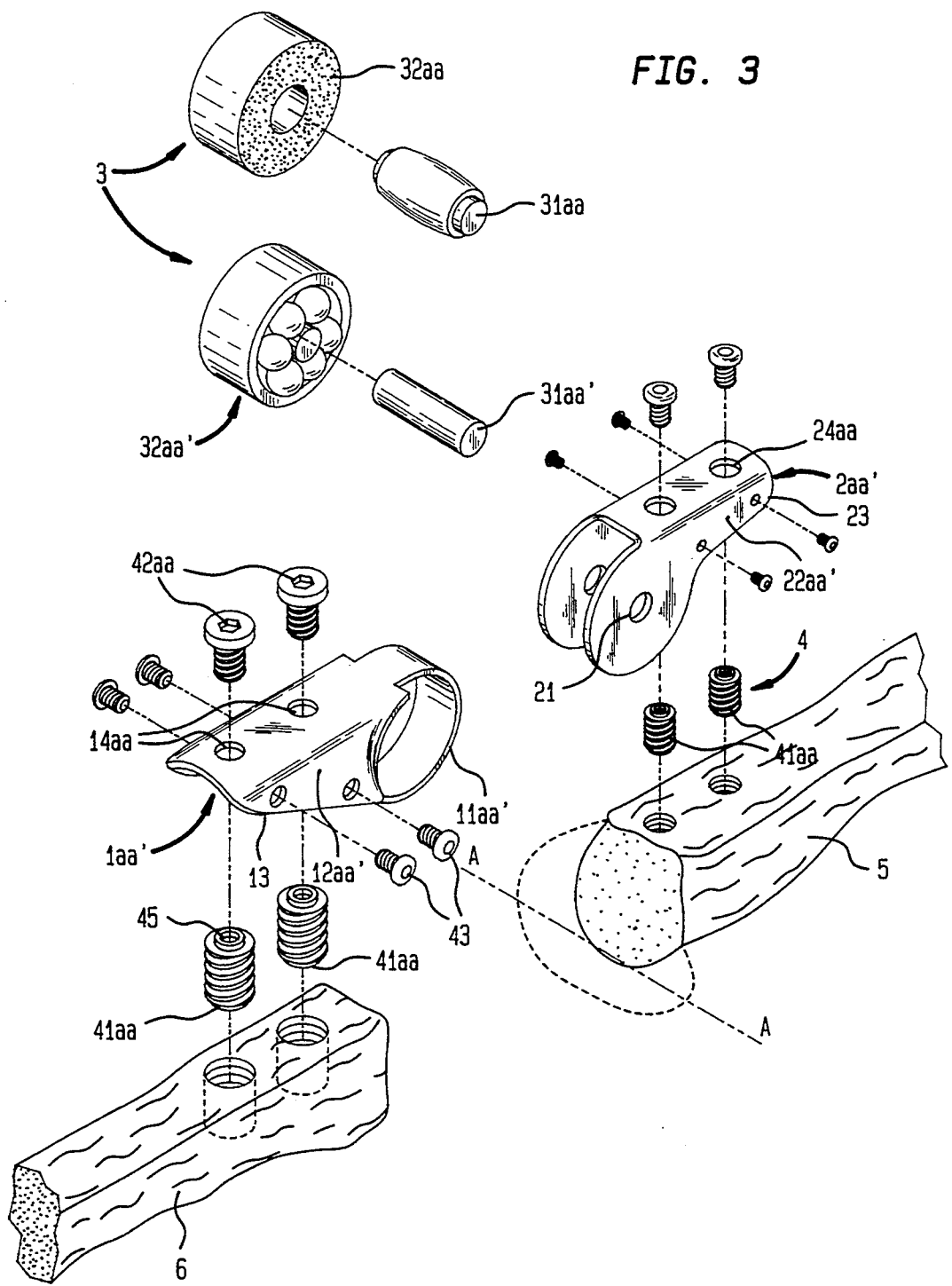
FIG. 3 shows an exploded view of a second embodiment of the invention.

FIG. 3 shows a second embodiment of the invention. Here, alternative means for attaching the distal part are shown, consisting of a band-shaped attachment part 12aa1 which is integral and surrounds a large part of the periphery of the bone shaft 6. Besides The securing screws 42aa which are fixed in the same way as described above, this prosthesis part is also secured with transverse screws 43 which are directly anchored in the cortex. The part 11aa1 surrounding the bearing can in this case either be connected to the attachment part 12aa1 of the prosthesis element at both its ends, or else consist of a one-side secured element 11aa1 which must then have great rigidity.

The proximal prosthesis element 2aa1 also has a similar attachment principle, and use is therefore also made here of transverse directly-anchored screws 43 which are arranged approximately at right angles to the securing screws 42aa which are intended to be screwed into the anchoring members 41aa.

Figure 4:
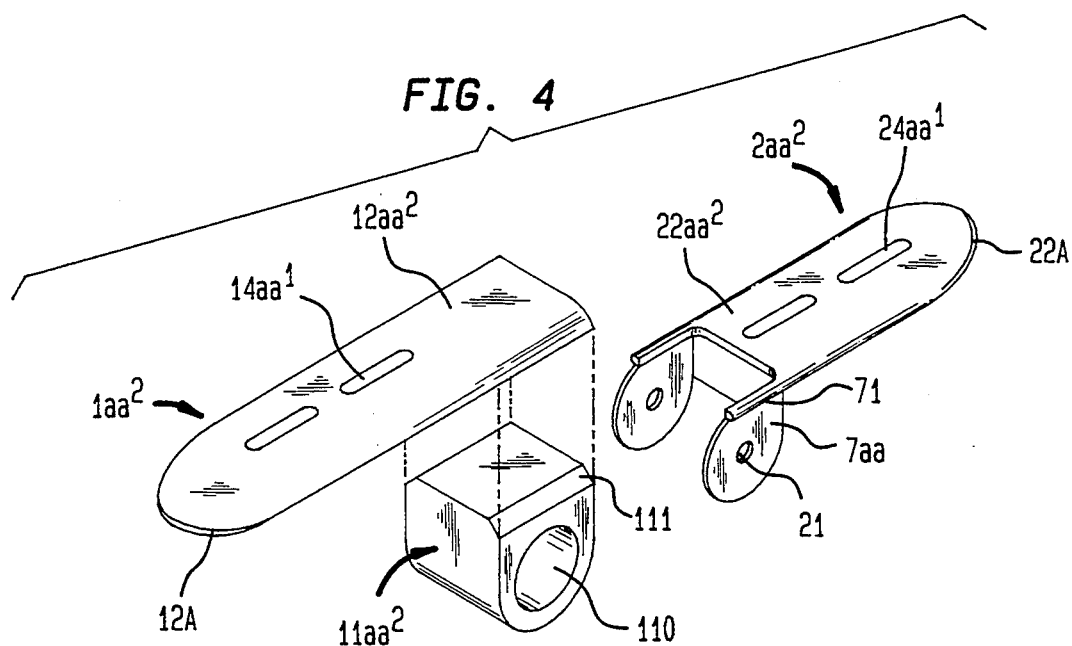
FIG. 4 shows an exploded view of a further embodiment.

FIG. 4 shows a further exemplary embodiment of an arrangement according to the invention. One change compared to what is described above is that component elements of each prosthesis part are here welded together. Thus, the figure shows a proximal prosthesis element 2aa2 consisting of an attachment part 22aa2 in the form of a plate which is connected to two flanges 7aa by means of welds 71. The flanges 7aa are provided with holes 21 which are intended to receive the axle ends of an axle element which is designed in accordance with the upper alternative shown in both FIGS. 2 and 3. The distal part 1*aa*1 is shown in the state in which it has not yet been welded together. The plate 12*aa*2 is arranged with two longitudinal bend lines 17, so that the edge areas of the plate 12*aa*2 have an angle corresponding to the angle of the bevelled surfaces 111 of the axle-fixing means 11*aa*2. The through hole 110 in the fixing means 11*aa*2 is intended for an axle element 31*aa*, 32*aa*. FIG. 4 also shows that those end surfaces 12A, 22A of the plates 12*aa*2 and 22*aa*2 respectively facing away from the joint are bevelled in such a way that they form a downward-directed pointed edge. This design is to reduce the friction against soft tissue.

Figure 5:
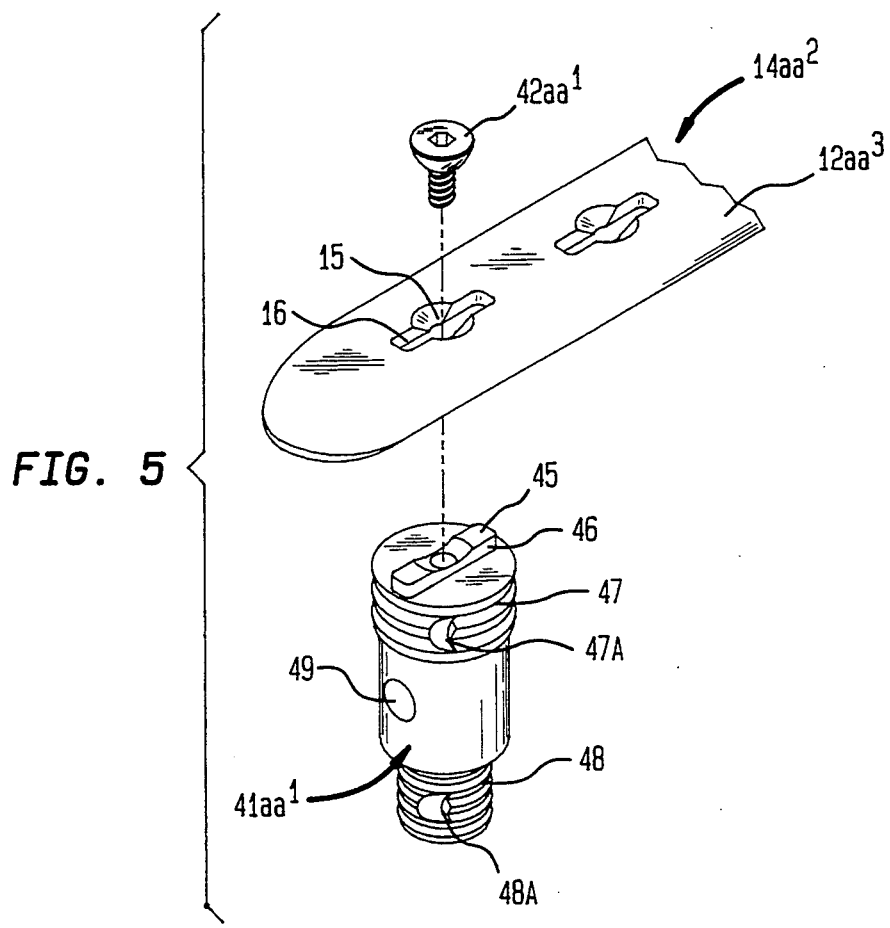
FIG. 5 shows the preferred embodiment of the anchoring element and the plate and screw cooperating with it.

FIG. 5 illustrates a possible embodiment of a plate 12*aa*3 for achieving lower friction against soft tissue. The last-mentioned aim is achieved by using countersunk screws 42*aa*1 (hexagonal socket cap) and by means of the fact that the holes 14*aa*1 in the plate are provided with conical recesses 15 which correspond to the conicity of the screw head 42*aa*1. In this way it is possible to obtain a fixing of the plate 12*aa*3 which does not have any components projecting above the upper surface of the attachment plate 12*aa*3. FIG. 5 also shows that the anchoring member 41*aa*1 is designed with a raised part 45, which on both sides has parallel opposite surfaces 46. The holes 14*aa*1 in the plate 12*aa*3 are also designed in a corresponding manner, that is to say with recesses 16 which correspond to the shape of the raised part 45. A more secure connection between the anchoring member 41*aa*1 and the plate 12*aa*3 can be obtained in this way. In order for it to be possible for the screw head 42*aa*1 to be screwed down to a level flush with the upper surface of the plate 12*aa*3, the raised part 45 is limited in terms of its height in relation to the thickness of the plate 12*aa*3, and the raised part 45 is designed with a conical depression. The recesses 46 on the raised part 45 further serve as bearings, for example for an open end wrench when the anchoring members 41*aa*1 are to be screwed into the bone. The figure also shows an expedient modification of the securing element 41*aa*1. The element is in fact designed with two different diameters in the threaded parts, in which respect the threaded part 47 which lies nearest the raised part 45 has a greater diameter than the lower part 48. Between the two threads 47, 48 there is a section provided with a hole 49, this section having a smooth outer surface. The hole 49, which is parallel to the bevels 46, serves as a channel for blood and medullary fluid. In order to be self-tapping, the threads are designed with slots 47A. The threads will preferably "take" simultaneously, which requires that securing elements 41*aa*1 with varying relative sizes should be prefabricated.

Figure 6:
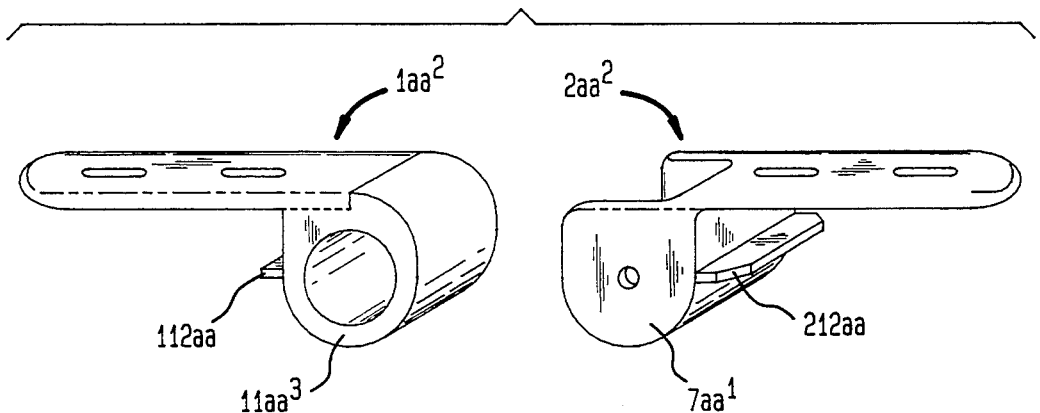
FIGS. 6 and 7 shows two embodiments in which the prosthesis elements also comprise parts projecting into the medullary cavity.

FIG. 6 shows a further modification of a joint prosthesis in accordance with the invention. The prosthesis parts shown are largely designed in the same way as those shown in FIG. 4 and described above. In addition, each prosthesis part 1*aa*2, 2*aa*2 is designed with tongue-like members 112*aa*, 212*aa* which are intended as positive locks at the ends of each bone shaft, by virtue of the fact that at least the proximal bone shaft is designed with a slit-shaped recess in towards the medullary cavity. The tongues 112*aa*, 212*aa* are advantageously welded securely on the respective part/parts 11*aa*3, 7*aa*1.

Figure 7:
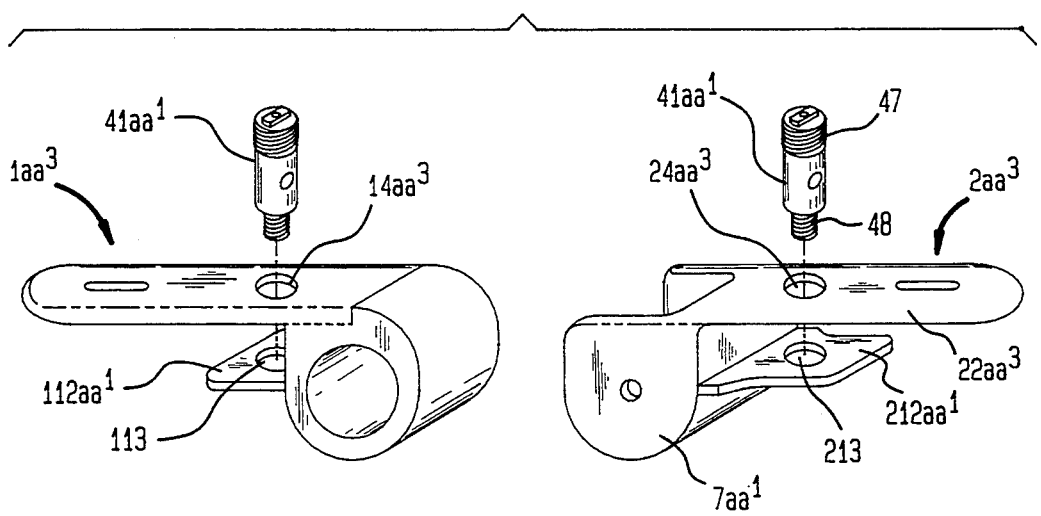

The embodiment in FIG. 7 moreover shows how the tongue-like members 112*aa*1, 212*aa*1 can be extended further into the medullary cavity and are in this case provided with a smooth-bored hole 113, 213 in line with the nearest fixture hole 14*aa*3, 24*aa*3 intended to cooperate with its respective fixture screw 41*aa*1. The diameter of these holes 113 and 213 corresponds to the diameter of the smooth section of the fixture screw 41*aa*1 situated between the threads 47, 48. These prosthesis parts are preferably implanted in a one-stage procedure, that is to say at the same time as the anchoring members 41*aa*1. The hole placed nearest the joint, and the hole 113 or 213 which is coaxial with it, is then penetrated during the operation by a direct-anchoring fixture screw 41*aa*1. The anchoring of the screw 41*aa*1 in the cortical parts is achieved with the aid of holes arranged in the bone tissue in a corresponding manner (different diameters). The plate 112*aa*1 on the proximal part 1*aa*3 can, if so desired, be introduced without any additional measures into the medullary cavity, since the joint head here has already been removed. At the distal part 2*aa*3, on the other hand, it is necessary, in accordance with the above, to create space for the plate 212*aa*1 by making a slit in the medullary cavity, a slit which is advantageously milled out with the aid of a fixture.

The invention is not limited to what is described above, but can be varied within the limits as have been set out in the following patent claims. It is thus possible to design the parts of the prosthesis in a number of biocompatible materials, such as pure titanium, titanium alloys, HD-polyethylene, a number of ceramics, etc. In addition, it is not necessary for the entire component to be made of this biocompatible material, and instead in many cases it is only necessary for its surface to be made of such a material, that is to say a "coated" component. As has already been mentioned, the joint is primarily designed to be used in connection with small joints of the finger-joint type, but it is also possible to use the prosthesis on joints of larger dimensions, such as knee- or elbow-joints. In such a case it is conceivable for only one prosthesis element, preferably the proximal one, to be anchored inside the medullary cavity of the bone shaft 5. In addition, and in particular in such a case, it is not necessary for all the anchoring members 41*aa*-4-1*aa*1 to be of the through type. The raised part 45 on the anchoring members 41*aa*-41*aa*1 can advantageously have other than a circular or partial-circle form, for example a rectangular form which possibly also gives even better guiding.

Moreover, the invention is not limited to the use of only one bearing member, but instead it is also conceivable to use two bearing members 32*aa*, and in this case the securing hollows 21 for the axle element 31*aa* would be arranged in a centrally positioned bracket, on the sides of which the two bearings would be arranged.

We claim:

1. A joint prosthesis adapted to permanently replace a natural articulated joint between distal and proximal bone shafts comprising:
   distal prosthesis means for connecting said joint prosthesis to the distal bone shaft;
   proximal prosthesis means for connecting said joint prosthesis to the proximal bone shaft, said distal and proximal prosthesis means including at least one longitudinally extending mounting member, each of the distal and proximal bone shafts having periosteal parts thereon, and at least one of the distal and proximal bone shafts including at least one generally transverse bore therein;
   articulated prosthetic joint means having a positive interlocking connector means arranged between said distal prosthesis means and said proximal prosthesis means for hingedly connecting said distal prosthesis means to said proximal prosthesis means; and securing means for securing said at least one longitudinally extending mounting member of said distal and proximal prosthesis means to the periosteal parts of respective ones of the distal and proximal bone shafts, wherein said at least one longitudinally extending member is sized to extend a greater distance along the respective distal or proximal bone shafts than any other portion of joint prosthesis, said at least one of said distal and proximal prosthesis means associated with a corresponding one of the distal and proximal bone shafts having at least one passageway extending therethrough for alignment with the at least one generally transverse bore, said securing means including anchoring means for insertion at least partially within the at least one generally transverse bore and structured to extend through said at least one passageway whereby said securing means can be permanently fixed to the corresponding one of the distal and proximal bone shafts.

2. The joint prosthesis of claim 1 wherein said securing means further comprises a plurality of securing screws, said anchoring means having threaded areas therein and being threadedly connected at said threaded areas to respective ones of said securing screws.

3. The joint prosthesis of claim 2 wherein said distal prosthesis means includes a first elongate side and a second elongate side opposing said first elongate side, said first elongate side being disposed for arrangement in assembled position adjacent a first side of the periosteal part of the distal bone shaft and said second elongate side being disposed for arrangement in assembled position adjacent a second side of the periosteal part of the distal bone shaft, said first side of the periosteal part opposing the second side of the periosteal part, said anchoring means being disposed for insertion within the at least one generally transverse bore between said first and second opposing sides of said distal prosthesis means and being disposed for alignment with a pair of said passageways thereof, and being threadedly mounted to a pair of said securing screws extending through respective ones of said pair of passageways.

4. The joint prosthesis of claim 2 further comprising friction reducing means for minimizing friction between said plurality of securing screws and soft tissue within a patient's body.

5. The joint prosthesis of claim 4 wherein said friction reducing means is arranged on said distal prosthesis means.

6. The joint prosthesis of claim 1 wherein said anchoring means have a generally cylindrical shape and include outer threads thereon so that said anchoring members can be securely fixed within said at least one generally transverse bore.

7. The joint prosthesis of claim 1 wherein said anchoring means comprise a plurality of anchoring members having a first end and a second end, at least one of said ends having a raised part thereon, said raised part being sized and shaped to extend at least partially through said at least one passageway to secure respective ones of said anchoring members in said distal and proximal prosthesis means.

8. The joint prosthesis of claim 1 wherein said securing means comprises a biocompatible material.

9. The joint prosthesis of claim 1 wherein said distal prosthesis means has a generally concave shape and is adapted to lie adjacent the periosteal part of the distal bone shaft.

10. The joint prosthesis of claim 1 wherein said proximal prosthesis means has a generally concave shape and is adapted to lie adjacent said periosteal part of said proximal bone shaft.

11. The joint prosthesis of claim 1 wherein said articulated joint means comprises an axle element arranged between said distal and proximal prosthesis means, and bearing means rotatably mounted on said axle element for facilitating relative movement pivotable of said distal and proximal prosthesis means.

12. The joint prosthesis of claim 11 wherein said proximal prosthesis means includes a first flanged sidewall and a second flanged sidewall opposing said first flanged sidewall, said first flanged sidewall having a first aperture therein, said second flanged sidewall having a second aperture therein aligned with said first aperture, said axle element being rotatably mounted in said first and second apertures whereby said axle element is linearly fixed with respect to said proximal prosthesis means.

13. The joint prosthesis of claim 11 wherein said distal prosthesis means includes a proximal end and a distal end and a curved bearing retaining means arranged adjacent said proximal end for rotatably retaining said bearing means therein, said bearing means being linearly fixed in said bearing retaining means with respect to said distal prosthesis means.

14. The joint prosthesis of claim 11 wherein said bearing means comprises a ball bearing device.

15. The joint prosthesis of claim 11 wherein said bearing means comprises a slide bearing device.

16. A joint prosthesis adapted to permanently replace a natural articulated joint between distal and proximal bone shafts comprising:

distal prosthesis means for connecting said joint prosthesis to the distal bone shaft;

proximal prosthesis means for connecting said joint prosthesis to the proximal bone shaft, said distal and proximal prosthesis means including at least one longitudinally extending mounting member, each of the distal and proximal bone shafts having periosteal parts thereon and including at least one generally transverse bore therein;

articulated prosthetic joint means having a positive interlocking connector means arranged between said distal prosthesis means and said proximal prosthesis means for hingedly connecting said distal prosthesis means to said proximal prosthesis means; and securing means for securing said at least one longitudinally extending mounting member of said distal and proximal prosthesis means to the periosteal parts of respective ones of the distal and proximal bone shafts, wherein said at least one longitudinally extending member is sized to extend a greater distance along the respective distal or proximal bone shafts than any other portion of joint prosthesis, said distal and proximal prosthesis means each having at least one passageway extending therethrough for alignment with respective ones of the generally transverse bores for receiving at least a portion of said securing means therein, said securing means including anchoring members for insertion at least partially within the generally transverse bores of the distal and proximal bone shafts and extending through respective ones of said passageways of said distal and proximal prosthesis means.

17. The joint prosthesis of claim 16 wherein said securing means further comprises a plurality of securing screws, said anchoring members having threaded areas therein and being threadedly connected at said threaded areas to respective ones of said securing screws, said anchoring members further having a generally cylindrical shape and including outer threads thereon so that said anchoring members can be securely fixed within respective ones of the generally transverse bores of the distal and proximal bone shafts.

18. The joint prosthesis of claim 16 wherein said securing means comprises a biocompatible material.

19. The joint prosthesis of claim 16 wherein said articulated joint means comprises an axle element arranged between said distal and proximal prosthesis means, and bearing means rotatably mounted on said axle element for facilitating articulatable relative movement of said distal and proximal prosthesis means.

20. The joint prosthesis of claim 16 further comprising friction reducing means for minimizing friction between said securing means and soft tissue within a patient's body.

* * * * *

UNITED STATES PATENT AND TRADEMARK OFFICE
CERTIFICATE OF CORRECTION

PATENT NO. : 5,443,516

DATED : August 22, 1995

INVENTOR(S) : Albrektsson et al.

Page 1 of 3

It is certified that error appears in the above-identified patent and that said Letters Patent is hereby corrected as shown below:

Column 4, line 16, "32aa1" should read --$32aa^1$--.
Column 4, line 18, "32aa1" should read --$32aa^1$--.
Column 4, line 20, "31aa1" should read --$31aa^1$--.
Column 4, line 23, "31aa1" should read --$31aa^1$--.
Column 4, line 24, "32aa1" should read --$32aa^1$--.
Column 4, line 43, "12aa1" should read --$12aa^1$--.
Column 4, line 44, "The securing" should read --the securing--.
Column 4, line 48, "11aa1" should read --$11aa^1$--.
Column 4, line 50, "12aa1" should read --$12aa^1$--.
Column 4, line 51, "11aa1" should read --$11aa^1$--.
Column 4, line 53, "2aa1" should read --$2aa^1$--.
Column 4, line 64, "2aa2" should read --$2aa^2$--.
Column 4, line 64, "22aa2" should read --$22aa^2$--.
Column 5, line 2, "1aa1" should read --$1aa^1$--.
Column 5, line 3, "12aa2" should read --$12aa^2$--.
Column 5, line 5, "12aa2" should read --$12aa^2$--.
Column 5, line 7, "11aa2" should read --$11aa^2$--.
Column 5, line 8, "11aa2" should read --$11aa^2$--.
Column 5, line 10, "12aa2" should read --$12aa^2$--.
Column 5, line 10, "22aa2" should read --$22aa^2$--.
Column 5, line 15, "12aa3" should read --$12aa^3$--.
Column 5, line 17, "42aa1" should read --$42aa^1$--.
Column 5, line 18, "14aa1" should read --$14aa^1$--.
Column 5, line 20, "42aa1" should read --$42aa^1$--.
Column 5, line 21, "12aa3" should read --$12aa^3$--.
Column 5, line 23, "12aa3" should read --$12aa^3$--.
Column 5, line 24, "41aa1" should read --$41aa^1$--.

UNITED STATES PATENT AND TRADEMARK OFFICE
CERTIFICATE OF CORRECTION

PATENT NO. : 5,443,516

DATED : August 22, 1995

INVENTOR(S) : Albrektsson et al.

It is certified that error appears in the above-identified patent and that said Letters Patent is hereby corrected as shown below:

Column 5, line 26, "14aa1" should read --$14aa_3^1$--.
Column 5, line 26, "12aa3" should read --$12aa_3^3$--.
Column 5, line 30, "41aa1" should read --$41aa_3^1$--.
Column 5, line 30, "12aa3" should read --$12aa_3^3$--.
Column 5, line 32, "42aa1" should read --$42aa_3^1$--.
Column 5, line 33, "12aa3" should read --$12aa_3^3$--.
Column 5, line 35, "12aa3" should read --$12aa_3^3$--.
Column 5, line 38, "41aa1" should read --$41aa_1^1$--.
Column 5, line 41, "41aa1" should read --$41aa_1^1$--.
Column 5, line 51, "41aa1" should read --$41aa_1^1$--.
Column 5, line 57, "1aa2" should read --$1aa_2^2$--.
Column 5, line 57, "2aa2" should read --$2aa^2$--.
Column 5, line 63, "11aa3" should read --$11aa^3$--.
Column 5, line 64, "7aa1" should read --$7aa^1$--.
Column 5, line 66, "112aa1" should read --$112aa^1$--.
Column 5, line 66, "212aa1" should read --$212aa^1$--.
Column 6, line 1, "14aa3" should read --$14aa_3$--.
Column 6, line 1, "24aa3" should read --$24aa^3$--.
Column 6, line 2, "41aa1" should read --$41aa_1^1$--.
Column 6, line 4, "41aa1" should read --$41aa_1^1$--.
Column 6, line 8, "41aa1" should read --$41aa^1$--.
Column 6, line 11, "41aa1" should read --$41aa^1$--.
Column 6, line 11, "41aa1" should read --$41aa^1$--.
Column 6, line 14, "112aa1" should read --$112aa^1$--.
Column 6, line 14, "1aa3" should read --$1aa_3$--.
Column 6, line 17, "2aa3" should read --$2aa^3$--.

UNITED STATES PATENT AND TRADEMARK OFFICE
CERTIFICATE OF CORRECTION

PATENT NO. : 5,443,516
DATED : August 22, 1995
INVENTOR(S) : Albrektsson et al.

It is certified that error appears in the above-identified patent and that said Letters Patent is hereby corrected as shown below:

Column 6, line 19, "212aa1" should read --$212aa^1$--.
Column 6, line 41, "1aa1" should read --$1aa^1$--.
Column 6, line 42, "41aa1" should read --$41aa^1$--.
Column 8, line 7, "said periosteal part of said" should read --the periosteal part of the--.
Column 8, line 13, "relative movement pivotable" should read --relative pivotable movement--.

Signed and Sealed this

Ninth Day of January, 1996

BRUCE LEHMAN

*Attest:*

*Attesting Officer*   *Commissioner of Patents and Trademarks*